United States Patent
Goudarzi et al.

(10) Patent No.: US 11,188,813 B2
(45) Date of Patent: Nov. 30, 2021

(54) HYBRID ARCHITECTURE SYSTEM AND METHOD FOR HIGH-DIMENSIONAL SEQUENCE PROCESSING

(71) Applicant: STC.UNM, Albuquerque, NM (US)

(72) Inventors: Alireza Goudarzi, Albuquerque, NM (US); Darko Stefanovic, Albuquerque, NM (US); Steven Wayde Graves, Santa Fe, NM (US); Daniel Kalb, Albuquerque, NM (US)

(*) Notice: Subject to any disclaimer, the term of this patent is extended or adjusted under 35 U.S.C. 154(b) by 891 days.

(21) Appl. No.: 15/909,918

(22) Filed: Mar. 1, 2018

(65) Prior Publication Data
US 2018/0253640 A1   Sep. 6, 2018

Related U.S. Application Data

(60) Provisional application No. 62/465,290, filed on Mar. 1, 2017.

(51) Int. Cl.
*G06N 3/04* (2006.01)
*G06N 3/08* (2006.01)
*G16H 50/20* (2018.01)

(52) U.S. Cl.
CPC ......... *G06N 3/0454* (2013.01); *G06N 3/0445* (2013.01); *G06N 3/088* (2013.01); *G16H 50/20* (2018.01)

(58) Field of Classification Search
CPC .... G06N 3/0454; G06N 3/0445; G06N 3/088; G16H 50/20
See application file for complete search history.

(56) References Cited

U.S. PATENT DOCUMENTS

| | | | | |
|---|---|---|---|---|
| 9,934,364 B1* | 4/2018 | Kumar | ............ | G16H 50/20 |
| 10,898,125 B2* | 1/2021 | Givon | ............ | G16H 50/20 |
| 2018/0068434 A1* | 3/2018 | Bronkalla | ............ | G16H 40/63 |
| 2018/0247715 A1* | 8/2018 | Kumar | ............ | G16H 50/20 |
| 2018/0310870 A1* | 11/2018 | Givon | ............ | A61B 5/4088 |

OTHER PUBLICATIONS

Lukosevicious, Mantas et al.; Reservoir Computing Trends; pp. 2-8. (Year: 2012).*
Goh, Hanlin et al.; Learning Deep Visual Representations; 191 pages. (Year: 2014).*
Chouikhi, Naima et al.; PSO-based analysis of Echo State Network parameters for time series forecasting; 2017 Elsevier; Applied Soft Computing 55 (2017) 211-225. (Year: 2017).*
Chouikhi, Naima et al.; Genesis of Basic and Multi-Layer Echo State Network Recurrent Autoencoder for Efficient Data Representations; pp. 1-13. (Year: 2018).*

(Continued)

*Primary Examiner* — Stanley K. Hill
(74) *Attorney, Agent, or Firm* — Valauskas Corder LLC

(57) ABSTRACT

The invention is directed to a hybrid architecture that comprises a stacked autoencoder and a deep echo state layer for temporal pattern discovery in high-dimensional sequence data. The stacked autoencoder plays a preprocessing role that exploits spatial structure in data and creates a compact representation. The compact representation is then fed to the echo state layer in order to generate a short-term memory of the inputs. The output of the network may be trained to generate any target output.

12 Claims, 7 Drawing Sheets

(56) References Cited

OTHER PUBLICATIONS

Vincent et al., "Stacked denoising autoencoders: Learning useful representations in a deep network with a local denoising criterion" J. Mach. Learn. Res., 11:3371-3408, 2010.
Deng et al., "Deep Learning: Methods and Applications." Foundation and Trends in Signal Processing, vol. 7, Nos. 3-4 (2013) 197-387, 2013.
Bengio et al., Representation Learning: A Review and New Perspectives. arXiv.org > cs > arXiv:1206.5538, 2014.

* cited by examiner (a) bouncing balls ($E^2$)

(b) bouncing balls $R^2$ (c) MNIST ($E^2$)

(d) MNIST $R^2$

HYBRID ARCHITECTURE SYSTEM AND METHOD FOR HIGH-DIMENSIONAL SEQUENCE PROCESSING

CROSS-REFERENCE TO RELATED APPLICATIONS

This application claims the benefit of U.S. Provisional Patent Application No. 62/465,290 filed Mar. 1, 2017, incorporated by reference.

STATEMENT REGARDING FEDERALLY SPONSORED RESEARCH OR DEVELOPMENT

This invention was made with government support under NIH GM-107805 awarded by the National Institutes of Health and NSF CDI-1028238 awarded by the National Science Foundation. The government has certain rights in the invention.

FIELD OF THE INVENTION

The invention relates generally to neural networks. More specifically, the invention is directed to a hybrid architecture that comprises a stacked autoencoder and a deep echo state layer for temporal pattern discovery in high-dimensional sequence data.

BACKGROUND OF THE INVENTION

Neural networks are directed to the development of computers that can deal with abstract and poorly defined problems. For example, computers are used to understand the context of speech or recognize facial features of people.

Neural networks include an input layer and an output layer. Neural networks may also include one or more hidden layers. As shown in FIG. 1, a neural network comprises one or more nodes or neurons, e.g., the output of one neuron can be the input of another neuron. In FIG. 1, circles are used to denote nodes of the network 50 and lines represent the flow of information from node to node. The leftmost layer is the input layer 50A, the rightmost layer is the output layer 50C, with the middle layer of nodes being the hidden layer 50B. Although FIG. 1 illustrates a network with a flow of information from left-to-right, other types of neural networks are contemplated, such as those with more intricate connections.

Deep recurrent neural networks are powerful systems for spatial and temporal pattern discovery and classification. While these systems have state-of-the-art performance in various machine learning tasks, they require a computationally expensive training, which limits their application, especially for temporal problems and sequence modeling.

Reservoirs are large fixed recurrent neural networks that can reconstruct a target output with adaptation only in the output layer. The computational power of reservoirs derives from stable embedding of temporal sequences in their short-term memory. Despite their fast training and excellent performance in time series computation, their applications have been restricted mainly to low-dimensional inputs, owing to their limited memory capacity. Despite its fast training and accurate time series processing capability, reservoir computing has been unpopular in the recent surge in deep learning and big data applications due to its limited short-term memory.

Signal processing based on reservoir computing (RC) consists of a fixed high-dimensional dynamical system driven with an input and a linear output layer. The input-dependent activity of the system is mapped to a target signal using the output layer. The approach was originally proposed as a simplified model of the prefrontal cortex of the brain and later implemented using spiking and real-valued recurrent neural network for time series computation and chaotic prediction. The power of RC is attributed to a short-term memory with the characteristic that for a network of size N the network states embed temporal sequences up to N prior time steps for uncorrelated inputs and super-linear memory for sparse input sequences. For networks with saturating nonlinearity the memory grows with $\sqrt{N}$. For high-dimensional input, the memory is shared between the inputs. Because of the memory limitation and because short-term memory cannot be used for temporal pattern discovery, RC has not been applied to large-scale high-dimensional inputs such as video. The only notable attempts are the use of large multilayer reservoir for speech recognition which used Mel Frequency Cepstral Coefficients (MFCC) of recorded voice as inputs and classified the phonemes. The system achieved comparable performance comparable with to state of the art methods but used up to N=20,000 nodes. Another notable hybrid RC work used RC states as inputs to a downstream restricted Boltzman machine (RBM) in an early attempt to lift the fixed-depth memory in RBM. This approach uses principal component analysis (PCA) for dimensionality reduction and shows impressive performance compared with conditional RBM. Recurrent RBM has also been successfully applied to sequence modeling.

It has been known that recurrent neural networks (RNN) are computationally universal. However, the difficulty of learning long-term dependencies with back-propagation has restricted their application in sequential data modeling. The use of specialized memory cells, improvements in training algorithms, and combining with temporal generative models have been successfully applied to large-scale temporal sequence learning problems. These methods fundamentally differ from RC and have a different goal: they tackle the general problem of discovering temporal dependencies in sequential data. RC, on the other hand, stores the most recent information in a sequence and leaves it to the output layer to use what it needs. While in principle RNN and long short-term memory (LSTM) approaches are able to do as well as RC in time series processing, their training takes a long time. There have been attempts to learn the recurrent connectivity in RC, but these worthwhile attempts deviate from the goal of RC, which is to use short-term memory. Short-term memory can be viewed as a type of temporal kernel and it has been previously suggested that although kernels may have limitations in learning dependencies—due to relying on the smoothness of the underlying manifold of the data —, they could be beneficial for learning problems if combined with learned representations using deep neural networks.

Basic RC architectures such as echo state networks (ESN) have difficulty in processing high-dimensional inputs. Echo state networks are recurrent neural network with limited adaptation which makes them computationally efficient. However, due to limited adaptation, their memory capacity is limited which restricts their application to only low-dimensional data.

Thus, there is a need for an architecture and methods that bring the power of RC to high-dimensional sequential tasks that can benefit from short-term memory. The invention satisfies this need.

SUMMARY OF THE INVENTION

The invention is directed to a hybrid model with "stacked" or compressive autoencoders and a deep reservoir layer for high-dimensional sequence processing. An autoencoder is an artificial neural network used to learn a representation (encoding) for a set of data, typically for the purpose of dimensionality reduction. The architecture according to the invention uses a deep feedforward network to encode compact representation of high-dimensional inputs, and a reservoir layer that generates a short-term memory of the compact representation. Deep or shallow decoders may be used to extract the spatiotemporal information from the reservoir and generate a target output.

According to the invention, the "stacked" or compressive autoencoders generate a compact representation of the inputs, while the reservoir encodes the temporal order of the compact representations.

More specifically, the hybrid architecture according to the invention uses stacked denoising autoencoders (AE) to generate a smooth low-dimensional manifold from high-dimensional sequential input. The low-dimensional data, or perceptions, feed into a reservoir that generates a short-term memory (STM) of the inputs. Outputs are modularly trained to perform prediction or other desired computation on the STM. The use of stacked denoising AE for dimensionality reduction is preferable over common techniques such as random projection (RP) and principal component analysis (PCA).

Single or multilayer decoders can be trained to compute a target output from the reservoir states. For tasks that benefit from short-term memory, this short-term memory architecture provides an efficient real-time processing system with a modular architecture and fast learning.

The stacked autoencoders are trained using layer-wise backpropagation of error with local de-noising, which makes them robust to distortions and helps to preserve locality of the compact representation. The echo state output can be trained with linear regression, which makes it resource-efficient. The invention achieves competitive performance in canonical high-dimensional sequence modeling tasks such as video prediction with a fraction of the cost of conventional recurrent neural network models. Moreover, different outputs may be trained independently for different pattern discovery tasks using the echo state network. Advantageously, the invention is reusable for a wide range for applications and lowers the cost of deploying recurrent neural networks.

According to the invention, the application of such a network may be used for high-resolution high-throughput object detection, localization, and classification in flow cytometry data. It is contemplated that reservoir computing can be "scaled up" for big data and video processing applications that may benefit from short-term memory (STM), and from fast and modular learning. With the high energy efficiency of the invention, it is contemplated the hybrid architecture may be used on devices with resource constraints, such as low-end computers, handheld systems, mobile phones, and embedded computers.

The architecture and methods of the invention perform high-dimensional sequence modeling and prediction in a low-cost and computationally efficient manner; this includes, video, voice, and language processing.

One advantage of the invention is the use of multilayer autoencoders trained to generate compressive representation of a high-dimensional input such that the reconstruction of the original input from the compressive representation is robust to distortions in the compressive representation.

Another advantage of the invention is that it preserves locality in the compressive space, i.e., inputs that are close to each other result in compressive representations that are also close to each other.

Another advantage of the invention is robustness and locality preservation, which maps a sequence of high-dimensional inputs to a smooth trajectory on low-dimensional manifold.

Another advantage of the invention is that a low-dimensional input drives a fixed recurrent neural network. With an output layer reading the information in the network state and mapping it to a target output, the target output can be directed to future states in the compressive representation which can be decoded to generate the prediction of the original input.

The invention and its attributes and advantages will be further understood and appreciated with reference to the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION

Figure 1:
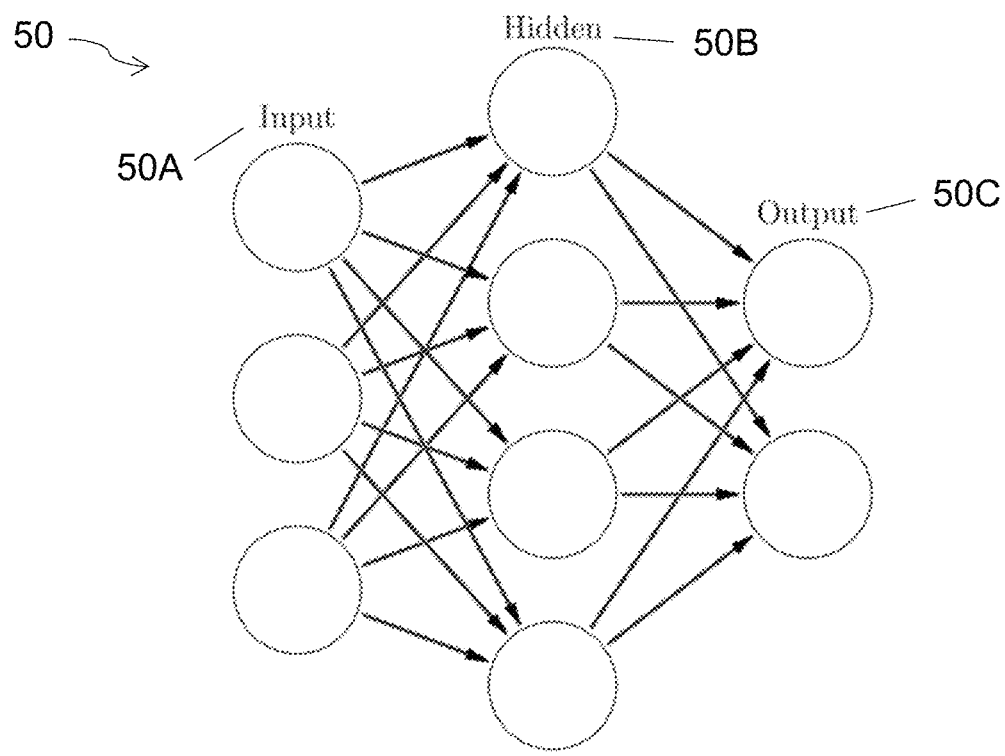
FIG. 1 illustrates a prior art neural network.

The invention is directed to a hybrid architecture based on deep denoising autoencoders and echo state networks for real-time processing of high-dimensional input. Despite accurate time series processing performance echo state networks (ESNs) have been limited to low-dimensional inputs owing to their limited capacity. The invention separates spatial and temporal correlation by first creating a low-dimensional representation of the data that is embedded in the short-term memory of echo state networks providing an alternative to recurrent neural network with fast and modular training. The use of autoencoders is fundamental to the success of the hybrid architecture as compared to previous attempts of scaling up echo state networks that used principal component analysis (PCA).

According to the invention, dimensionality of an input is reduced and fed to a downstream echo state network (ESN), a popular reservoir computing architecture. ESN has been shown to have excellent ability for real-time processing, even for chaotic time series prediction. However, fixed recurrent connections and short-term memory limit its ability to discover temporal dependencies and process high-dimensional inputs. Two conditions are required for this dimensionality reduction to maintain the generality of the architecture for different applications. First, the low-dimensional embedding preserves locality, and second, the embedding provides good reconstruction of original input even from a corrupted representation. The former condition ensures the consecutive data points of the original input fall on a smooth low-dimensional manifold and the latter condition permits application of the architecture for input prediction tasks, for example, reconstructing the prediction for the inputs from the prediction of the latent representation on the low-dimensional manifold.

To describe the operation of the hybrid architecture (not the implementation of the architecture), the notion of an autoencoder AE consists of a pair of parameterized functions: an encoder $f_\theta$ that maps its input space $\mathcal{U} \subset \mathbb{R}^n$ to a latent space $\mathcal{H} \subset \mathbb{R}^z$ and a decoder $g_{\theta'}$ that maps the latent space to an output space $Y \subset \mathbb{R}^m$. The dimensionality of inputs, latent, and output spaces are specified by u, h, and y respectively and they may be superscripted, e.g., $u^i$ to distinguish between instances, or they can be presented as a function of time, e.g., u(t). The overall AE function is denoted by $g_{\theta'}(f_\theta(u))=g_{\theta'} \circ f_\theta(u)$. For multilayer AE, compatible pairs of $f$ and $g$ are indexed with i, e.g., $g_{\theta'_1}^1 \circ g_{\theta'_2}^2 \circ f_{\theta'_2}^2 \circ f_{\theta'_1}^1(u)$ are two stacked AEs. This is not to be confused with the absolute index of each layer denoted by l. The sum-of-squares is used to denote the error or distance between two multidimensional vectors as follows, $\|x-y\|^2 = \Sigma_i (x_{(i)} - y_{(i)})^2$, with i iterating over the dimensions of the vectors. The architecture according to the invention also incorporates a recurrent neural network whose instantaneous states represent a sequence of prior inputs from a preceding encoder function $f$ with this representation denoted with $\rho(t, f(u(0)), \ldots, f(u(t)))$.

Autoencoders (AE) are multilayer neural networks that learn a compact representation of input in their hidden layers such that using a local denoising algorithm in training AEs can result in learning a useful high-level representation of data which can improve the performance of a downstream classifier. According to the invention, stacked AE layers generate the desired output from the state of the recurrent network. The layers are indexed $l = \{1, \ldots, L\}$ and the connectivity between layers $l_0$ and $l_1$ is denoted by weight matrices $W_{l_0, l_1}$. The reservoir layer is denoted by $l = r_0$. The architecture of decoder depends on the desired task. It could be a single or a multi-layer network with linear, softmax, or other saturating nonlinearities.

Figure 2:
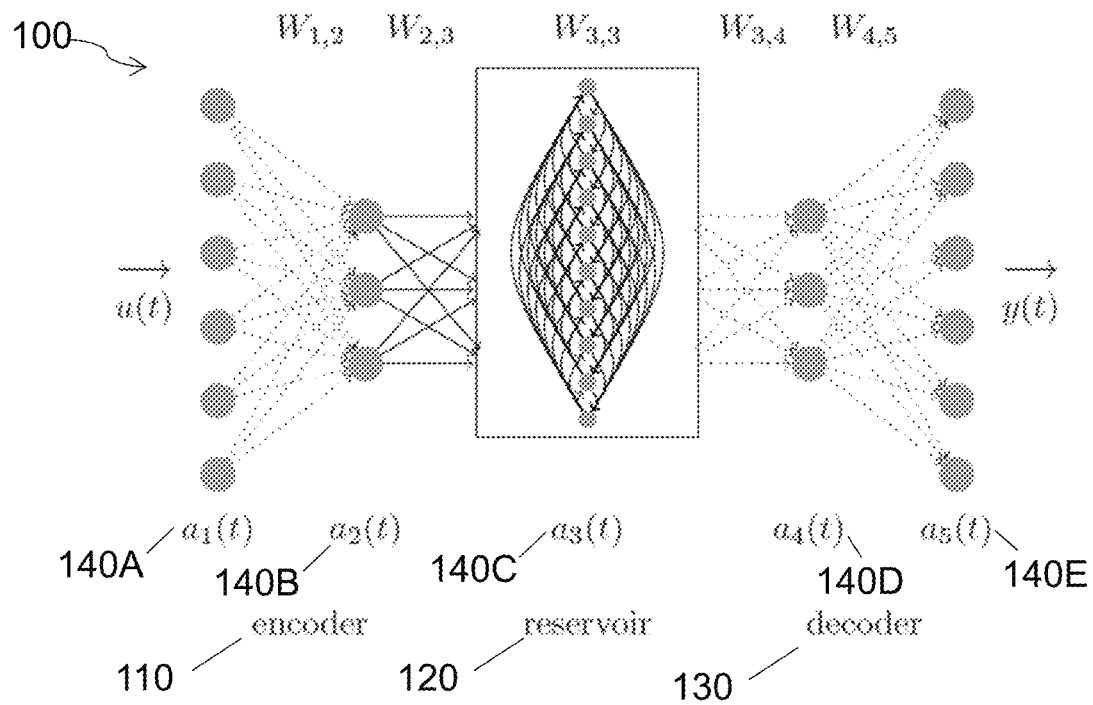
FIG. 2 illustrates a hybrid architecture according to the invention.

FIG. 2 shows a network architecture 100 of a hybrid autoencoder model. The architecture 100 includes an encoder 110, deep reservoir layer 120 and a decoder 130. The model comprises or consists of $l = \{1, \ldots, L\}$ layers and L-1 weight matrices $W_{l_0, l_1}$ connecting layer $l_0$ to $l_1$. The reservoir layer $l = r_0$ has an additional weight matrix for its recurrent connections $W_{r_0, r_0}$. As shown in FIG. 2, solid connections are initialized and fixed, and dotted connections are learned during training. The encoder 110 produces low-dimensional representation of the data, the reservoir layer 120 creates a short-term memory, and the decoder 130 generates the output using the reservoir states.

More specifically, the ESN in the middle reservoir layer 120 is fed a perception of the input video frames generated from the encoder 110, and it uses a linear output trained to predict the perception of the next frame of the video, which in turn is converted to an actual prediction for the future frame using a second layer. Although FIG. 2 is applicable for next frame prediction of video input, any application is contemplated.

At every time step t the activation of each layer $a_l(t)$ during a forward pass of the network is given by:

$$a_l(t) = \begin{cases} u(t), & l = 1 \\ f_l(W_{l-1,l} a_{l-1}(t)), & l \neq r_0 \\ f_l(W_{l,l} a_l(t-1) + W_{l-1,l} a_{l-1}(t)), & l = r_0 \end{cases}$$

The activation function of each layer l is denoted by $f_l$ since feedforward, reservoir, and output layer usually have distinct activation functions. The first layer l=1 is directly connected to input u(t) as shown by 140A. FIG. 2 also illustrates layer 140B as part of the encoder 110. The reservoir layer 120 is the third layer 140C. The activation of the other layers except for the reservoir layer $l = r_0$ is given by the multiplication of the activation of the previous layer and the weight matrix $W_{l-1,l}$. The reservoir layer 120 activation is computed with a combination of the activation of the preceding layer $l = r_0 - 1$ and the reservoir activation at the previous time step. The decoder 130 includes a fourth layer 140D and a fifth, or output layer 140E.

Although it would be possible to train the parameters of the proposed model $W_{l_0, l_1}$ by treating the entire model as a single monolithic network and back-propagating the error from the output across the reservoir all the way to the first layer, this approach would have to deal with various challenges of back-propagation. Instead, modular training is used to exploit the greedy layer-wise pre-training approach and the fixed input and recurrent weights in ESNs. With this approach the encoder weights, i.e., the weights from the first layer up to one layer prior to the reservoir, can be trained using the layer-wise pre-training algorithm with local denoising. This training is independent of the task and serves only to produce a suitable representation of the input. The decoder weights, i.e., the weights after the reservoir layer, are trained depending on the task described more fully below.

Figure 3:
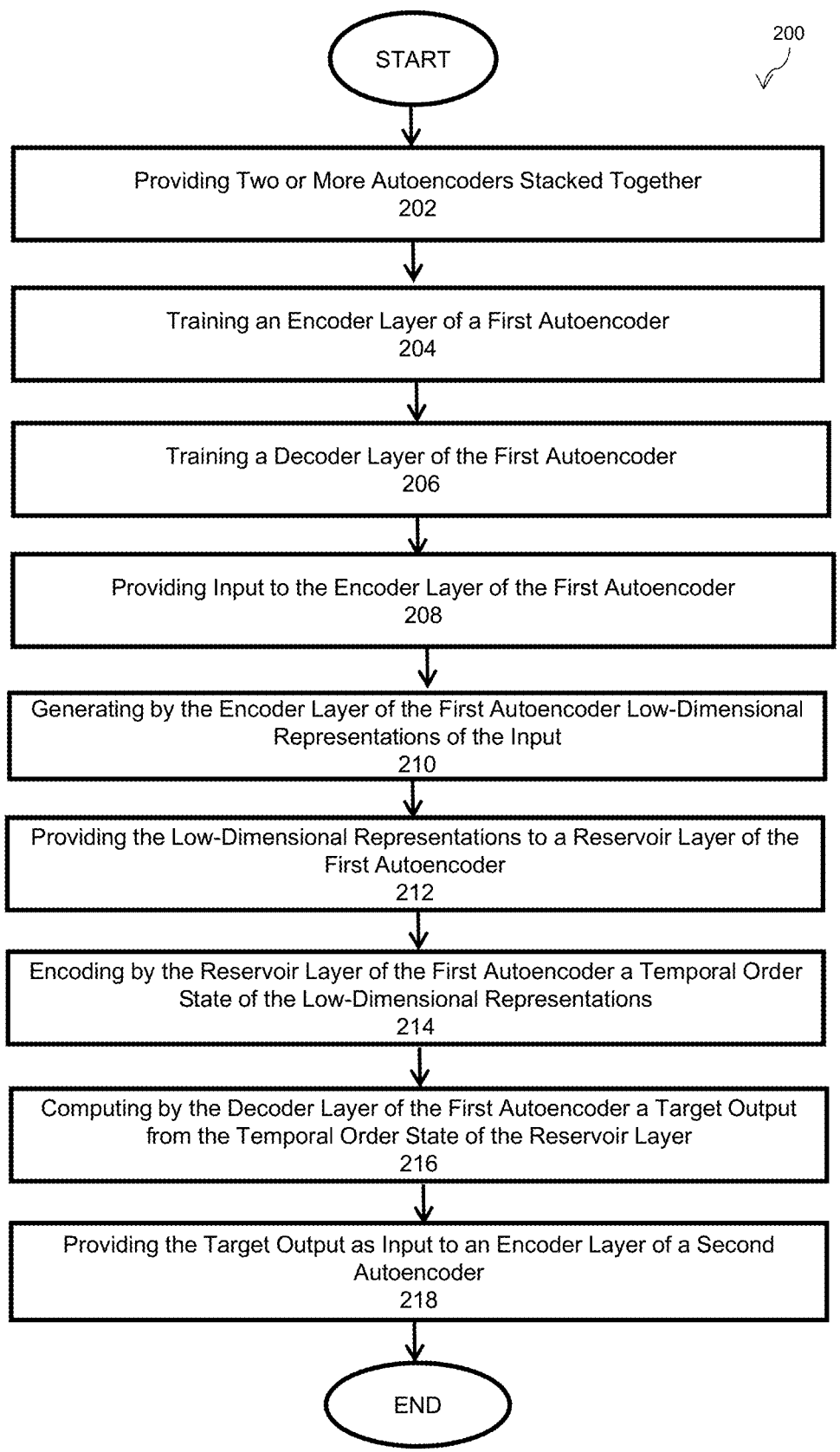
FIG. 3 is a flow chart of the steps performed for processing of high-dimensional input according to the invention.

FIG. 3 is a flow chart of the steps performed for processing of high-dimensional input according to the invention.

Assuming the inputs u(t) are from the space $U \subset \mathbb{R}^n$ and target outputs y(t) are from the space $\mathcal{Y} \subset \mathbb{R}^n$, for the purpose of modular training at each layer, the desired activation at the layer is denoted by $\hat{a}_l(t)$.

Two or more stacked encoders are provided at step 202. The encoder comprises or consists of layers before the reservoir $l < r_0$ and their associated parameters $W_{l-1,l}$. The encoder is trained at step 204 to generate a suitable low-dimensional representation of the input. According to the invention, in each autoencoder the signal from the encoder passes through the inner autoencoder and then is fed to the decoder, except for the innermost autoencoder in which the signal from the encoder passes through the intermediary ESN. According to the invention, the signal from the system input passes through a series of stacked encoders, and then through the intermediary ESN, and then through a series of stacked decoders to system output. Any autoencoder is contemplated, however the invention with be described with respect to the denoising AE as described in Vincent et al. "Stacked denoising autoencoders: Learning useful representations in a deep network with a local denoising criterion." *J. Mach. Learn. Res.*, 11:3371-3408, 2010, incorporated by reference. Hence given an input space $\mathcal{U}$ the algorithm aims to find a representation function of the inputs $f_\theta(\mathcal{U})$ used to reconstruct the input $g_{\theta'}(f_\theta(\mathcal{U}))$ accurately. To do this, samples of the input $u \in \mathcal{U}$ are drawn and stochastically corrupted forming $\bar{u} \in \mathcal{U}$. The corrupted samples $\bar{u}$ are then used in an optimization:

$$\underset{\theta,\theta'}{\mathrm{argmin}} \mathcal{L}(u, g_{\theta'}(f_\theta(\bar{u})))$$

where $$\mathcal{L}(x, y) = \frac{\Sigma_i \|x_i - y_i\|^2}{2}$$

is the loss function. In a neural network implementation of this encoder the parameters $\theta$ and $\theta'$ are weight matrices connecting the input to the hidden layer and the hidden layer to the output. To illustrate, an embodiment of the invention directed to a network with three layers, $\theta = W_{1,2}$ and $\theta' = W_{2,3}$. Weights are trained using the stochastic gradient descent (SGD). Intuitively, because during the training $f_\theta$ is generated from corrupted inputs, the parameters are trained to extract high-level useful information about the input that represent the input in a generic task independent way. Hence a reason why the denoising AE is chosen for dimensionality reduction. The denoising AE can be used in hierarchies with each successive layer of the hierarchy generating higher-level representation of the input.

Architecture and training the decoder requires task-specific considerations at step 206. In general, a single or multilayer network can be used to take inputs from reservoir state space $\mathcal{R}$ and produce output in the target space $\mathcal{Y}$, i.e., $f: \mathcal{R} \rightarrow \mathcal{Y}$. Because the reservoir encodes information in short-term memory, the pairs of instantaneous reservoir states and target outputs $(a_{r_0}(t), \hat{y}(t))$ are all that are needed for this training. There is no need to preserve the order of these pairs. Hence the ordinary SGD and LBFGS with randomized mini-batches can be used to train the decoder.

At step 208, an input is provided to the first encoder. At step 210, the encoder generates a low-dimensional representation of the input. This input is provided to the reservoir layer at step 212. The reservoir layer includes an intermediary ESN. The ESN is a recurrent neural network with a sparsely connected hidden layer (typically 1% connectivity). The connectivity and weights of hidden neurons are fixed and randomly assigned. The weights of output neurons can be learned so that the network can (re)produce specific temporal patterns. The reservoir layer encodes a temporal order state of the low-dimensional representations at step 214. The decoder computes a target output from the temporal order state of the reservoir layer at step 216. At step 218, the target output may be provided as input to an encoder of a second stacked autoencoder, with its own intermediary ESN in the reservoir layer.

There are situations where the decoder training can be broken down into simpler steps, for example, recalling prior inputs, classification of prior inputs, prediction of inputs, and training for multiple tasks.

With respect to recalling prior inputs, a 2-layer decoder is contemplated. The parameters of the first layer are given by the weight matrix $W_{r_0,r_0+1}$ that can be trained using known ESN training to reconstruct the inputs of the reservoir from t time steps ago. That is, layer $r_0+1$ has linear activation function $f_{r_0+1}(x)=x$ and the weights are trained using linear regression to produce the target $\hat{a}_{r_0+1}(t)=a_{r_0-1}(t-\tau)$, the inputs to the reservoir layer from its preceding layer at time $t-\tau$. Hence the weights trained during the encoder training can be used to reconstruct $u(t-\tau)$ from $a_{r_0-1}(t-\tau)$.

For classification of prior inputs, regular pre-training can be used along with fine tuning of denoising AE to train a classifier. The layers prior to the classifier can be used as the encoder feeding the extracted features or perceptions of the input to the reservoir layer. A linear output can be trained to recover the perceptions and the pre-trained classifier can be used as the final layer.

Prediction of inputs brings the power of ESN for predicting smoothly varying time series to high-dimensional inputs, e.g., video input. When the input is limited to one or a few dimensions, the plain ESN may provide accurate predictions of the input, particularly for inputs that lie on a smooth manifold. Denoising AE can be trained on high-dimensional inputs to generate encoding and decoding layers for use with the hybrid architecture according to the invention. During pre-training, the order of the input does not matter. After training, the weights can be used as an encoder to generate low-dimensional perceptions of the input. Input is fed through the encoder in order. The encoder results in activations $a_{r_0-1}(t)$ which are fed to the reservoir. The readout from the reservoir is trained to generate the predictions for the inputs, i.e., $\hat{a}_{r_0+1}(t)=a_{r_0-1}(t+\tau)$. The decoder weights from the AE training can be used to generate prediction of the raw inputs from $a_{r_0+1}(t)$.

With respect to training for multiple tasks, a distinct advantage of ESNs is that because the input and recurrent connection are fixed, new readout layers can be trained to perform additional desired processing without influencing the result of previously trained output layers. In the hybrid architecture too, as many decoders as necessary may be added for additional tasks without affecting the previously trained decoders, because the encoder is not modified after the initial training.

The central purpose of using AE in the hybrid architecture according to the invention is to reduce the dimensionality of input. Many dimensionality reduction algorithms exist that could be implemented more efficiently than a deep AE, such as random projection (RP) and principal component analysis (PCA). However, the invention is advantageous in that dimensionality reduction has accurate reconstruction (the original input is accurately reconstructed from the latent representation), robustness to distortion (reconstruction of a target output should be robust to distortion in the latent representation), and locality preservation (the relative distance of data points in the input space should be preserved in the latent space).

These properties are crucial for the hybrid architecture. ESNs are particularly powerful in prediction of time series in which sequential data points $u(t)$ lie on a smooth manifold. This power comes from their ability to embed sequences in short-term memory, which is akin to Takens' delay-coordinate embedding, but it preserves the geometry of the original time series in addition to its topology. Reducing input dimensionality helps apply ESN to high-dimensional sequences such as video data. However, in general, reduction of dimensionality does not preserve locality, meaning two neighboring points of the input space, i.e., $\|u_0-u_1\|^2<\sigma$, may be far apart in the low-dimensional space, $\|f_\theta(u_0)-f_\theta(u_1)\|^2 \nless C\sigma$ for any two constants $\sigma$ an $C>1$ and the low-dimensional projection $f_\theta(u)$.

For example, RP, a standard dimensionally reduction technique, may manifest many properties of deep learning systems and may preserve locality to some extent but this may not be enough. As shown and described below, RP in fact has poor locality preservation compared with PCA and AE. This is due to the regulatory effect of training with noise in smoothing the functional space that contains the operator $f$ and its influence in learning suitable representations in deep AE.

Another key factor is the accurate reconstruction of the output in the face of noisy latent representation. Despite the research on the effect of training with noisy input, further research is needed into the effect of noise in latent layers of a deep AE on reconstruction performance. Indeed, the normal approach in training and applying AE does not necessitate such a study. However, it is crucial for decoding layers to be robust to noise in hidden layers during operation. To illustrate this, without loss of generality, consider a 5-layer structure with the reservoir on layer $r_0=3$.

For brevity, the low dimensional representation generated by the second layer at time t with $f_t$, the history-dependent reservoir states at time t with $\rho_t$ as a shorthand for $\rho(t, f(u(0)), \ldots, f(u(t)))$, the immediate layer after the reservoir with $g_t^2$ and the output layer with $g_t^1$. In a video prediction scenario, the parameters of $g_t^2$ are trained to produce a prediction for $f_{t+1}$ from $\rho_t$. The parameters of $g_t^1$ are the output parameters trained during the AE training and are duals of the $f_t$ parameters, i.e., they can produce the original input from the low-dimensional representation $f_t$. The predictions of $g_t^2$ are, however, lossy, depending on the quality of $h_t$ and $g^1$. Therefore $g_t^2 \circ h_t$ can be viewed as a noisy communication channel between $f_t$ and $g_t^2$. Due to the noisy training, $g_t^1 \circ f_t$ is expected to be robust to the noise in inputs u(t). Results of experiments on noisy latent representation are discussed more fully below.

An autoencoder network learns a representation (encoding) for a set of data, typically for the purpose of dimensionality reduction. The network according to the invention may be implemented according to an exemplary distributed system as seen in FIG. 4 with FIG. 5 illustrating a more detailed block diagram of a client node.

Figure 4:
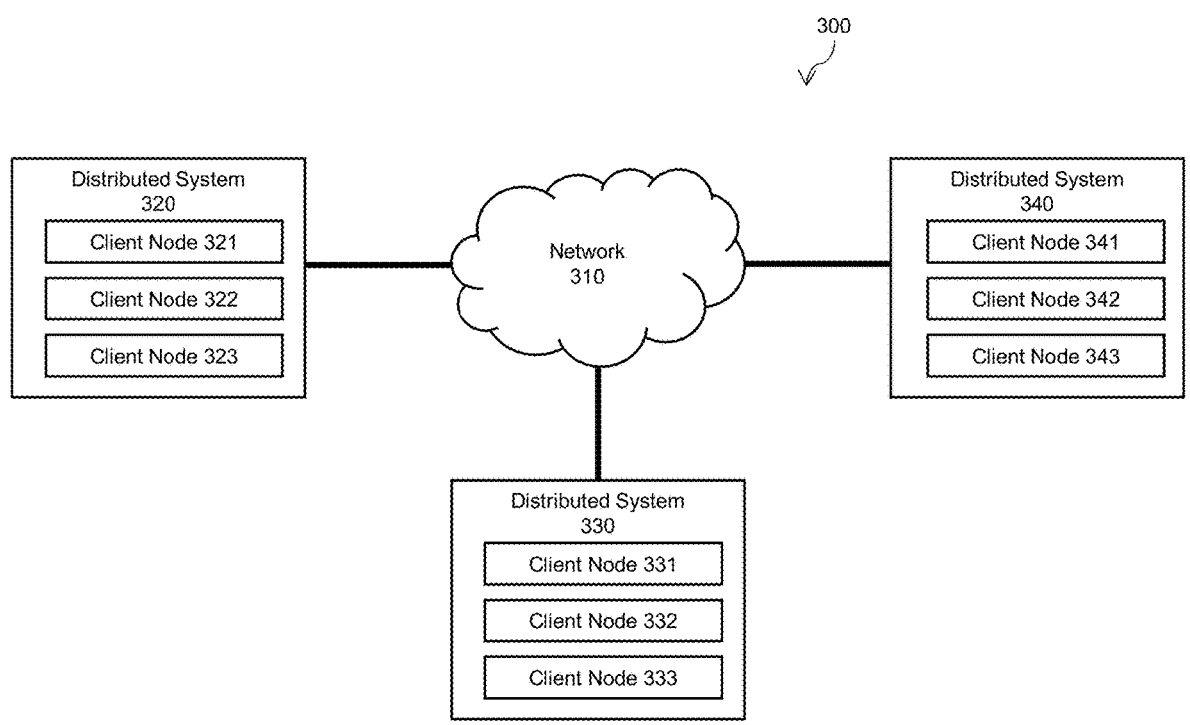
FIG. 4 illustrates an exemplary distributed system according to the invention.

The exemplary distributed system 300 shown in FIG. 4 includes a network 300 that interconnects one or more distributed systems 320, 330, 340. Each distributed system includes one or more client nodes. For example, distributed system 320 includes client nodes 321, 322, 323; distributed system 330 includes client nodes 331, 332, 333; and distributed system 340 includes client nodes 341, 342, 343. Although each distributed system is illustrated with three client nodes, one skilled in the art will appreciate that the exemplary distributed system 300 may include any number of client nodes.

Figure 5:
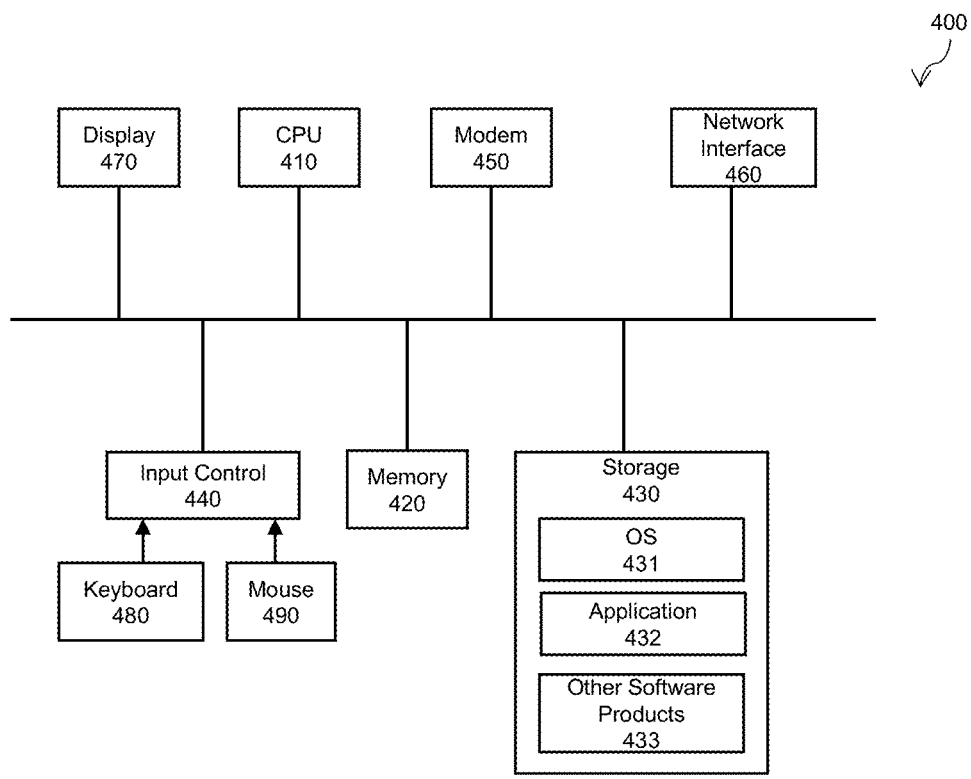
FIG. 5 illustrates a more detailed block diagram of a client node illustrated in FIG. 4.

FIG. 5 is an exemplary client node in the form of an electronic device 400 suitable for practicing the illustrative embodiment of the invention, which may provide a computing environment. One of ordinary skill in the art will appreciate that the electronic device 400 is intended to be illustrative and not limiting of the invention. The electronic device 400 may take many forms, including but not limited to a workstation, server, network computer, Internet appliance, mobile device, a pager, a tablet computer, and the like.

The electronic device 400 may include a Central Processing Unit (CPU) 410 or central control unit, a memory device 420, storage system 430, an input control 440, a network interface device 460, a modem 450, a display 470, etc. The input control 440 may interface with a keyboard 480, a mouse 490, as well as with other input devices. The electronic device 400 may receive through the input control 440 input data necessary for performing functions in the computing environment. The network interface device 460 and the modem 450 enable an electronic device to communicate with other electronic devices through one or more communication networks, such as Internet, intranet, LAN (Local Area Network), WAN (Wide Area Network) and MAN (Metropolitan Area Network). The communication networks support the distributed execution of the job. The CPU 410 controls each component of the electronic device 400. The memory 420 fetches from the storage 430 and provides instructions to the CPU 410. The storage 430 usually contains software tools for applications. The storage 430 includes, in particular, code for the operating system (OS) 431 of the device 400, code for applications 432 running on the system, such as applications for providing the computing environment, and other software products 433, such as those licensed for use with or in the device 400.

Following is a demonstration of the application power of the hybrid architecture according to the invention, for example, on a number of synthetic tasks such as symbolic computations on visual input, next frame prediction of video input, and particle detection in high-throughput imaging.

To illustrate the improvements of the invention, the locality preservation and robustness of denoising AE, RP, and PCA are examined without an intermediary ESN. Locality preservation and robustness are also examined for the architecture according to the invention. In addition, the architecture is applied to synthetic and real-world tasks. The intermediary ESN is a simple ESN with a ring topology and identical weights. The input weights are randomly assigned from {-1, +1} with Bernoulli distribution. The size of the network, spectral radius and the magnitude of inputs weights change depending on the task. The output layer is trained using SGD or linear regression depending on the task.

Turning first to locality preservation, it is determined whether perceptions generated by denoising AEs preserve locality of data points in the input space. A 3-layer AE is considered with z the size of the hidden layer, i.e., the dimensionality of the hidden state space. Parameters θ and θ' are trained to minimize the reconstruction error $\|g_{\theta'}(f_\theta(u))-u\|^2$. The optimization is done using SGD with learning rate 0.75 and momentum 0.5, batch size 100, and 1000 epochs. The data is 10,000 randomly chosen inputs from datasets that include the MNIST (Modified National Institute of Standards and Technology database) dataset or frames (15×15) of three bouncing ball videos.

The dimensionality reduction results are compared between AE with hidden layer size z={9, 16, 25, 36, 49, 64} and masking fraction $m_f=0.5$. The masking fraction is a per-pixel probability of corrupting the input by setting its value to zero. Then for randomly sampled $u_i, u_j \in U$ the distance is defined as $E_u^2(k)=\|u_i-u_j\|^2$ and $E_{f(u)}^2(k)=\|f_\theta(u_i)-f_\theta(u_j)\|^2$ for k={1, ..., K}. The coefficient of determination $R^2$ between $E_u^2(k)$ and $E_{f(u)}^2(k)$ is the proxy for how well the hidden layer preserves the locality.

The distance between the inputs is a good predictor of the distance between the hidden representations. A perfect locality preservation results in $R^2=1$ and no preservation results in $R^2=0$. The results are compared with PCA using the states with the z largest coefficients in the principle component space. RP with a random matrix is also used to reduce the dimensionality of the inputs to z and calculate the $R^2$ between the distance of random points in low-dimensional space and the input space. The average sum-of-squared errors $\langle E^2 \rangle = \Sigma_k \|g_{\theta'}(f_\theta(u_k))-u_k\|^2$ is also reported, where $f_θ(u)$ is the hidden representation and $g_{θ'}(f_θ(u))$ is the reconstruction of the input for the hidden representation.

Figure 6:
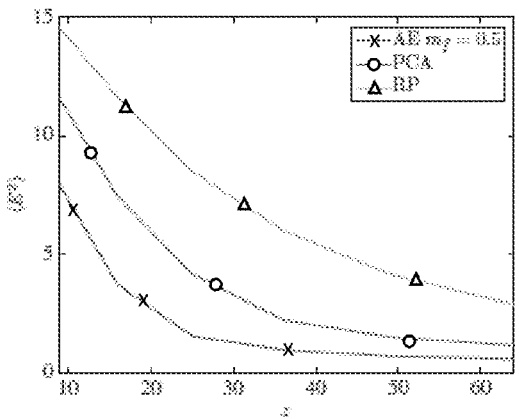
FIG. 6 illustrates graphs of reconstruction error and coefficient of determination between pairs of latent representations and their corresponding raw inputs.
Figure 6:
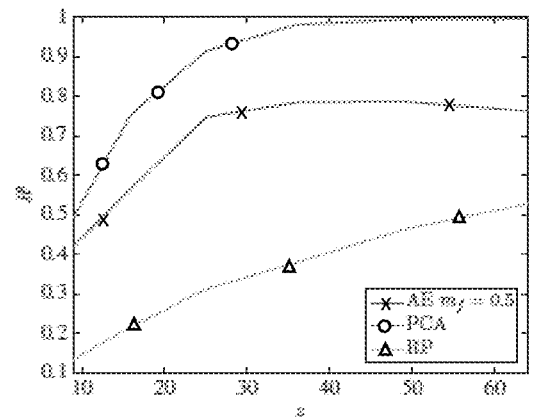
Figure 6:
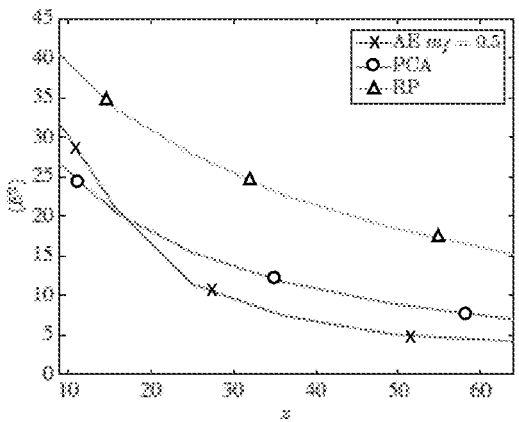
Figure 6:
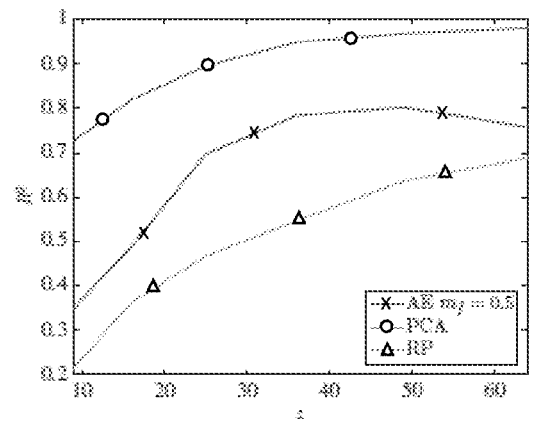

FIG. 6 illustrates the results—reconstruction error $\langle E^2 \rangle$ and coefficient of determination between pairs of latent representations and their corresponding raw inputs for randomly chosen inputs from predefined datasets, here MNITS and bouncing ball datasets. As can be seen, PCA achieves perfect locality preservation but high reconstruction error, RP gives high reconstruction error and loss of locality, while denoising AE gives the best reconstruction error and relatively high locality preservation.

Now the robustness of input reconstruction of a trained denoising AE by introducing noise to the latent representation is reviewed.

The results are compared with the robustness of the reconstruction in RP and PCA. This is done by sampling K data points from the inputs and calculating the average sum-of-squared errors $E=\Sigma_k \|g_{θ'}(f_θ(u_k)+σ_k)-u_k\|^2/K$, where $f_θ(u)$ is the latent representation, $g_{θ'}(f_θ(u))$ is the reconstruction of the input from the latent representation, and $δ_k$ is a noise vector. The elements of $δ_k$ are sampled from a uniform distribution on the interval $[0,α]$. For AE, the parameters $θ$ and $θ'$ are computed during training. For PCA, $θ'$ is the eigenvector of the covariance matrix of the inputs and $θ=θ'^{-1}$. To reconstruct the inputs from low-dimensional representation in the principal component space, z dimensions corresponding to the z largest eigenvalues of the covariance matrix are selected and multiplied by the corresponding columns of $θ'$. For RP, the parameter $θ$ is a n×z random matrix. The $θ'$ is calculated by the pseudoinverse solution to the equation $θ'f_θ(u)=u$.

Figure 7:
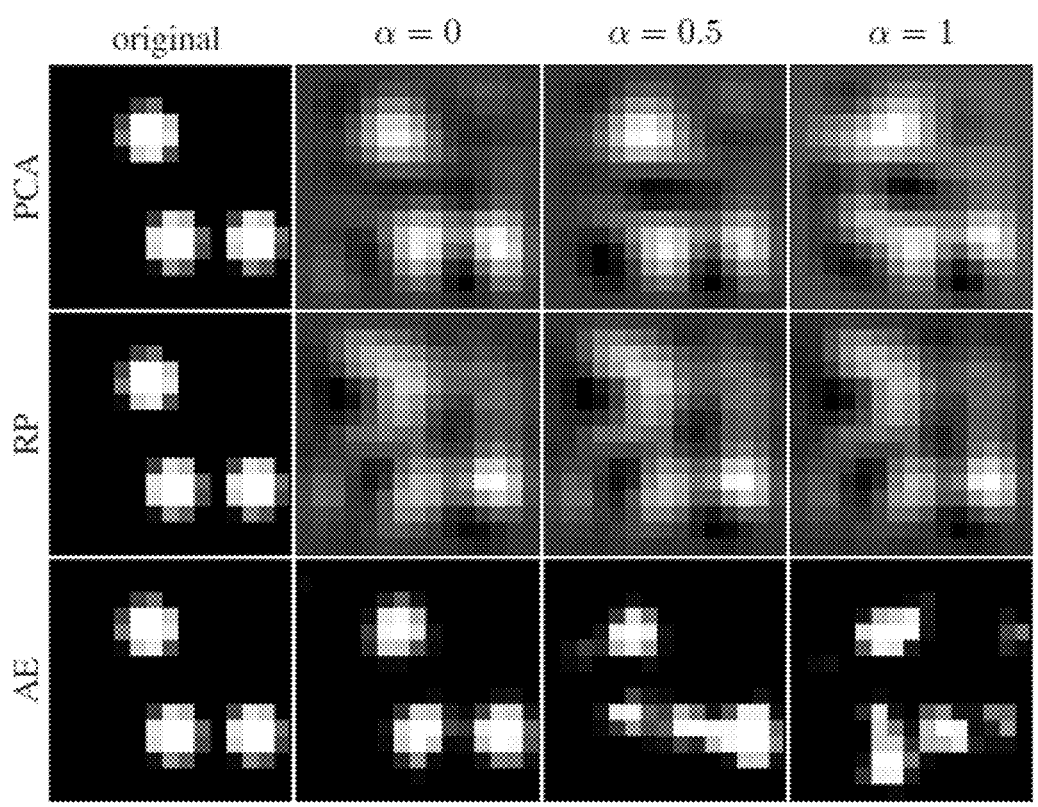
FIG. 7 illustrates representations of reconstructions of a sample image.

FIG. 7 shows the reconstruction of a sample image. As shown, the reconstruction is from the bouncing ball dataset. The latent representations of size z=9 and z=25 are generated with PCA, RP, and AE and corrupted with different levels of noise. AE shows a better reconstruction with and without noise.

Figure 8:
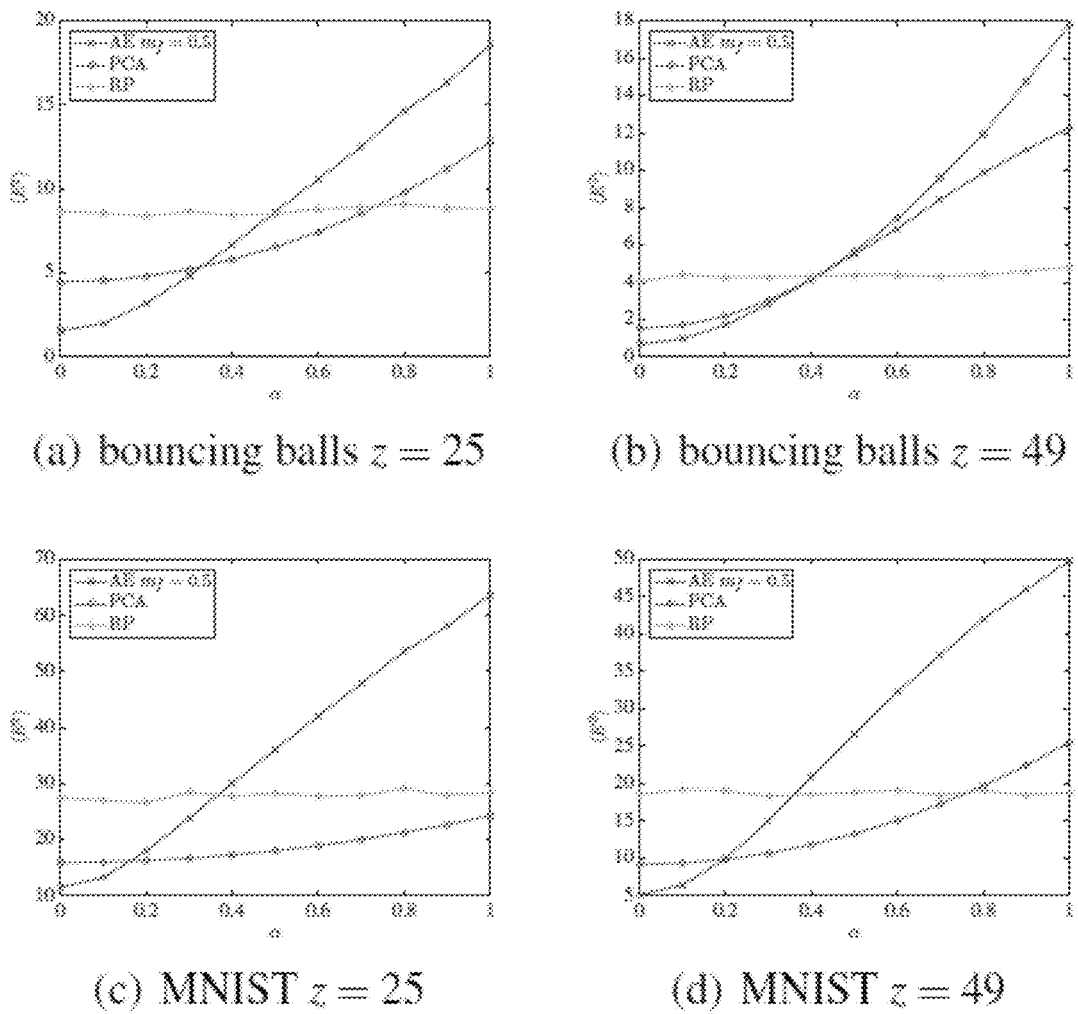
FIG. 8 illustrates graphs of reconstruction error from noisy latent representations of inputs.

FIG. 8 shows a systematic study of robustness for different values of noise intensity α. As seen, there is a clear distinction between the robustness behavior of the different dimensionality reduction models on the two datasets. This is because the MNIST dataset is a very sparse dataset in the sense that most of the fluctuations are located in the middle of the image. The fluctuations in the bouncing ball dataset are distributed over the entire image, because the balls move around freely. In this sense the bouncing ball dataset is very dense. For moderate noise, AE is the most robust. For high noise level, PCA gives better robustness for the MNIST dataset. But, given enough hidden nodes, e.g., z=49, AE is more robust on the denser, bouncing-ball images. RP in general gives poor robustness, but it is interesting that it is not sensitive to noise level.

The architecture is tested on the canonical example of bouncing ball prediction. This is a simple task but it suitably illustrates prediction of high dimensional sequences that describe smooth motion. It is also widely used and allows the comparison between the invention and alternative architectures. Sequences of 15×15-pixel frames of 3 bouncing balls are generated. Each pixel value is between 0 and 1. Each sequence is 31 frames long and the task is to predict the 31st frame after observing the first 30 frames. A 7-layer architecture is used with the following configuration: 225-64-25-147-25-64-225. The 5 middle layers combined consist of 300 nodes. The ESN has 147 nodes with spectral radius λ=0:5 and input weight coefficient v=0:001. The ESN activation function is tan h(x). The AE configuration 225-64-25-147-25-64-225 is trained using 5000 frames for training, 500 epochs of pre-training with learning rate 0.75, momentum 0.5, masking fraction 0.5, and 2,000 epochs fine tuning with learning rage 0.25. The weights are then used in the encoder and decoder layer of the hybrid architecture. ESN was trained on 1000 sequences and test the prediction on another 1000 sequences and achieve a cross-entropy error of 23.5 after training 226×300+301×300+301×225=225,825 parameters on $4 \cdot 10^4$ sequences. Although slightly higher error was registered, 226×64+65×25+148×25+26×64+6+5×225=36,078 parameters on 5000 frames for AE training versus 1000 sequences for ESN training.

Applying the invention to the application for high throughput particle detection in visual flow cytometry data, data is captured by a high-speed camera at rate of 25,000 frames per second. There are six bead populations with distinct fluorescent markers. The particles flow through a tube and pass inside a flow cells that focus them in predefined location. A laser light shines at the same location. The camera is set to capture images of the same location at high rate. When particles pass by the laser light they fluoresce, which is captured by the camera. The images are 8×2048 pixels with 14 bits per pixel. They are subsequently gated to 8×30 pixel wide images focused on where the particle passes. They are then max pooled to form a 1×30 pixel wide image of a single frame and normalized to have pixel values between [0,1].

The challenges of the dataset include: 1) because of high rate of the camera several images of the same particle is captured as it passes by the camera and 2) the particles vary widely in pixel intensity and the dimmest particles may merge with the background intensity, and 3) the high rate of capture creates artifacts in the images that can be mistaken with an actual particle.

It is noted that currently these images are processed manually by scientists and proper rules for determining when and what type of particles have been detected are hard-coded in a system that is widely used in medical diagnosis.

Figure 9:
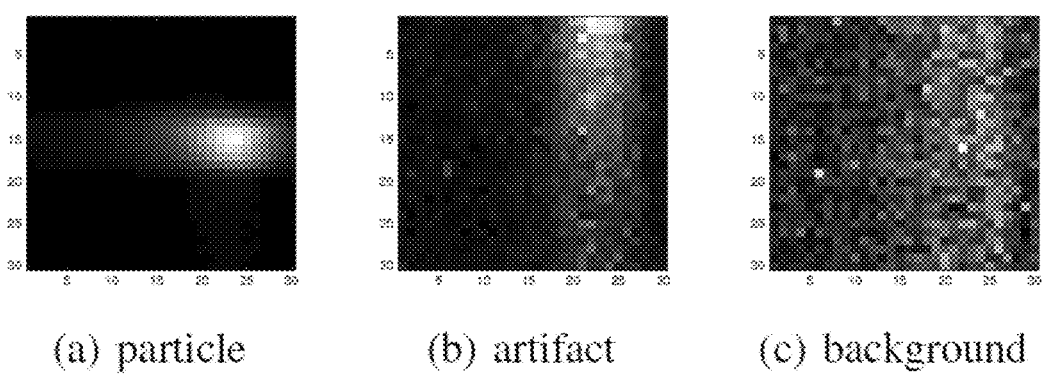
FIG. 9 illustrates pixel frames created by a sliding window over the post-processed images.

Automatic pattern discovery with deep neural network is an approach that may be applied in different domains of application. The hybrid architecture according to the invention efficiently trains particle detectors for this visual flow cytometry system. Pixel frames (30×30) are created by stacking 30 post processed images. The frames are slid down the dataset to create visual representation of the particles as shown in FIG. 9.

The dataset consists of 750,000 frames. The autoencoder is trained with 16 hidden nodes to reconstruct images in the dataset that have a $\ell_2$ norm >0.1. Majority of images below this norm are only background intensity. The network trained on all images will discard particles as noise. The frames from the whole dataset are then feed in sequence through the encoder and passed to an ESN with N=200 nodes, with spectral radius λ=0:8 and input coefficient v=0.1. The output is trained to generate 1 after seeing a particle. The system is essentially trained to track the particle and count the event after the particle has left the frame. The output training used linear regression using a sequence of 19,000 frames to train the output and test it on another 19,000 frames. Particles can be detected with 99% efficiency. The background intensity is cleanly filtered out by the encoder and does not interfere with the dim particles.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A hybrid architecture system for high-dimensional sequence processing, comprising:
   an autoencoder generating a compressive representation of a high-dimensional input using a neural network,
   an intermediary reservoir layer generating a low-dimensional manifold using an echo state network, wherein the autoencoder comprises an encoder layer and a decoder layer, each layer with a same number of hidden nodes, and the intermediary reservoir layer comprising interconnected nodes, the interconnected nodes connecting the hidden nodes of the encoder layer with the hidden nodes of the decoder layer.

2. The hybrid architecture according to claim 1, wherein the hybrid architecture predicts the next frames in a video clip.

3. The hybrid architecture according to claim 2, wherein the hybrid architecture classifies objects and their motion detected in the video clip.

4. The hybrid architecture according to claim 1, wherein the hybrid architecture performs a visual analysis for medical diagnosis.

5. The hybrid architecture according to claim 4, wherein the visual analysis is particle detection and classification and particle properties are determined on a particle by particle basis.

6. The hybrid architecture according to claim 1, wherein an activation a of each layer l at every time step t of a neural network is given by $a_l(t)$ according to:

$$a_l(t) = \begin{cases} u(t), & l = 1 \\ f_l(W_{l-1,l}a_{l-1}(t)), & l \neq r_0 \\ f_l(W_{l,l}a_l(t-1) + W_{l-1,l}a_{l-1}(t)), & l = r_0 \end{cases}$$

$f_l$ represents an activation function of each layer l,
u(t) represents the input to the neural network,
$W_{l-1,l}$ represents a weight matrix of the connectivity between layers, and
$r_0$ represents the intermediary reservoir layer.

7. The hybrid architecture according to claim 1, wherein the autoencoder is a plurality of stacked autoencoders.

8. A hybrid architecture method for processing high-dimensional sequences comprising the steps of:
   providing two or more autoencoders stacked together, wherein each autoencoder includes an encoder layer and a decoder layer;
   positioning a reservoir layer in the middle of the two or more autoencoders;
   training the encoder layer of the first autoencoder;
   training the decoder layer of the first autoencoder;
   providing an input to the encoder layer of the first autoencoder;
   generating by the encoder layer of the first autoencoder a low-dimensional representation of the input;
   providing the low-dimensional representations to the reservoir layer;
   encoding by the reservoir layer a temporal order state of the low-dimensional representations;
   computing by the decoder layer of the first autoencoder a target output from the temporal order state; and
   providing the target output as input to an encoder layer of a second autoencoder.

9. The hybrid architecture method according to claim 8 further comprising the steps of:
   performing an activation a of each layer l at every time step t given by $a_l(t)$ according to:

$$a_l(t) = \begin{cases} u(t), & l = 1 \\ f_l(W_{l-1,l}a_{l-1}(t)), & l \neq r_0 \\ f_l(W_{l,l}a_l(t-1) + W_{l-1,l}a_{l-1}(t)), & l = r_0 \end{cases}$$

$f_l$ represents an activation function of each layer l,
u(t) represents an input to a neural network,
$W_{l-1,l}$ represents a weight matrix of connectivity between layers, and
$r_0$ represents the reservoir layer.

10. A hybrid architecture system for high-dimensional sequence processing, comprising:
   a plurality of stacked autoencoders generating a compressive representation of a high-dimensional input,
   an intermediary reservoir layer generating a low-dimensional manifold using an echo state network, wherein each stacked autoencoder of the plurality comprises an encoder layer and a decoder layer, each layer with a same number of hidden nodes, and the intermediary reservoir layer comprising interconnected nodes, the interconnected nodes connected to an innermost stacked autoencoder of the plurality.

11. The hybrid architecture system for high-dimensional sequence processing according to claim 10, wherein the hidden nodes of the encoder layer of the innermost stacked autoencoder of the plurality are connected to the intermediary reservoir layer, which in turn is connected to the hidden nodes of the decoder layer of the innermost stacked autoencoder.

12. The hybrid architecture system for processing high-dimensional inputs according to claim 10, wherein each layer is activated according to an activation function:

$$a_l(t) = \begin{cases} u(t), & l = 1 \\ f_l(W_{l-1,l}a_{l-1}(t)), & l \neq r_0 \\ f_l(W_{l,l}a_l(t-1) + W_{l-1,l}a_{l-1}(t)), & l = r_0 \end{cases}$$

wherein a represents an activation of each layer l at every time step t of a neural network and is given by $a_l(t)$, $f_l$ represents the activation function of each layer l, u(t) represents the high-dimensional input to the neural network, $W_{l-1,l}$ represents a weight matrix of connectivity between layers, and $r_0$ represents the intermediary reservoir layer.

* * * * *